United States Patent [19]

Strickman et al.

[11] Patent Number: 4,630,602
[45] Date of Patent: Dec. 23, 1986

[54] DISPOSABLE CONTRACEPTIVE CERVICAL BARRIER

[76] Inventors: Melvyn B. Strickman, R.D. 1, Lawrence Rd., Bridgeton, N.J. 08302; Erick-Pierre Fournier, 30 Park Ave., New York, N.Y. 10016

[21] Appl. No.: 594,933

[22] Filed: Mar. 29, 1984

[51] Int. Cl.⁴ .............................................. A61F 5/46
[52] U.S. Cl. .................................. 128/127; 128/138 R
[58] Field of Search ................ 128/127, 138 R, 132 R

[56] References Cited

U.S. PATENT DOCUMENTS

| | | | |
|---|---|---|---|
| 2,079,022 | 4/1937 | Martin | 128/127 |
| 2,324,656 | 7/1943 | Vincent | 128/127 |
| 3,060,931 | 10/1962 | Clark | 128/127 |
| 3,216,422 | 11/1965 | Steiger et al. | 128/127 |
| 4,200,090 | 4/1980 | Probish | 128/127 |
| 4,304,226 | 12/1981 | Probish et al. | 128/127 |
| 4,311,543 | 1/1982 | Strickman et al. | 128/127 |

*Primary Examiner*—Robert P. Swiatek
*Assistant Examiner*—John G. Weiss

*Attorney, Agent, or Firm*—Duffield & Lehrer

[57] ABSTRACT

A disposable contraceptive cervical barrier includes a bowl-shaped thin flexible member and a substantially thicker circular rim unitary with the flexible member. The rim provides a spring tension effect for helping to maintain the barrier in position. A plurality of cavities are formed in the rim and are equidistantly spaced therearound. The cavities are open so as to be capable of receiving and holding a quantity of a spermicide. Alternatively, the flexible member itself can be provided with a plurality of grooves for holding the spermicide. Preferably, the barrier is made from a mixture of a hydrophilic foam polymer and a more conventional polyurethane polyether prepolymer-catalyst system. The mixture is molded in a closed mold having a volume of about ten percent of the volume which the material would occupy if allowed to foam freely. The finished product is similar to an elastomer except that internally it has a dense cellular structure and is bounded by an impermeable skin.

7 Claims, 9 Drawing Figures

FIG. 1
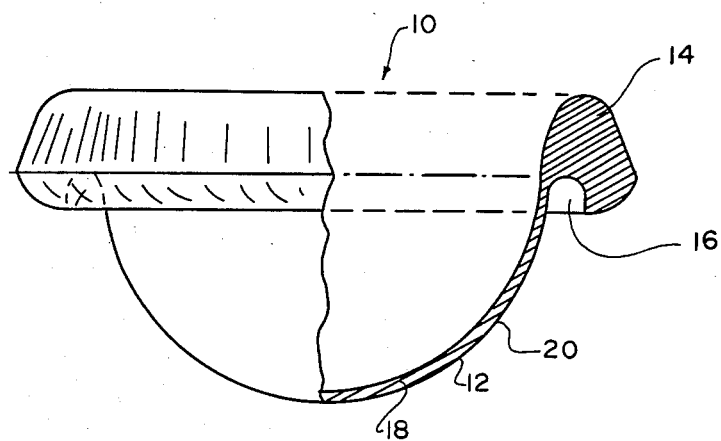
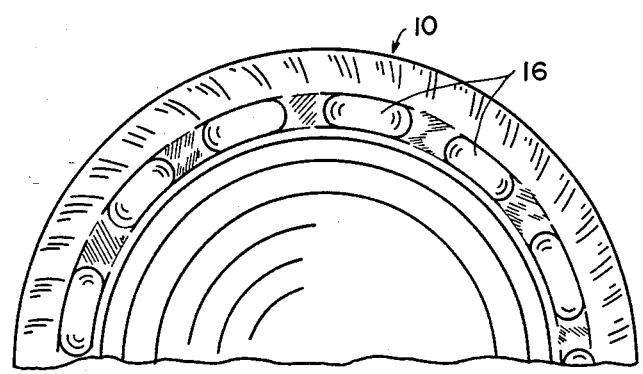
FIG. 2
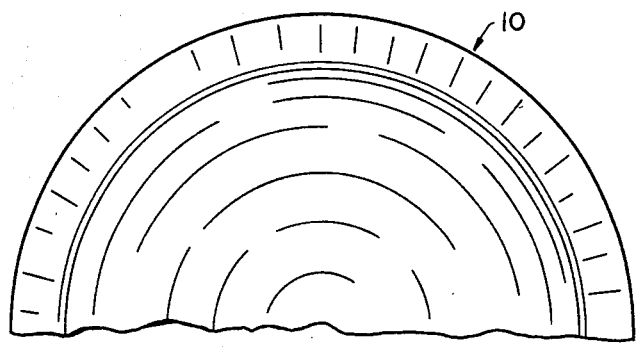
FIG. 3

FIG. 4
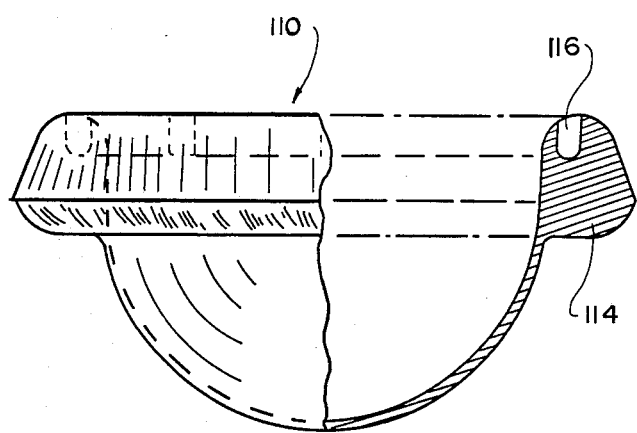
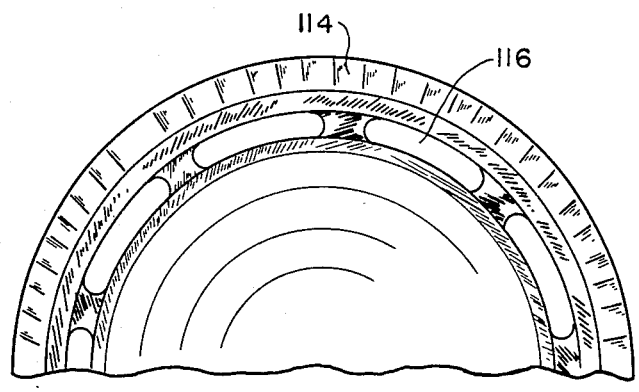
FIG. 5

DISPOSABLE CONTRACEPTIVE CERVICAL BARRIER

BACKGROUND OF THE INVENTION

The present invention is directed toward a disposable contraceptive cervical barrier and more particularly toward such a device which includes improved means for retaining a supply of a spermicide. The invention is also directed toward a method of making a disposable contraceptive cervical barrier and the use of novel materials for doing so.

Contraceptive cervical barriers such as diaphragms, cervical caps and other pessaries have been known and used for many years as a method of birth control. Until recently, such devices were intended to be used numerous times and, therefore, had to be made of relatively expensive elastomeric material. Furthermore, in order to make the rim of the barrier flexible yet have a spring tension effect, it was necessary to include a ring insert therein which added to the expense.

While the cervical barrier by itself provides some protection since it constitutes a physical barrier to sperm, it is customary to utilize a spermicide cream or gel with such devices. This is normally done by applying a thin layer of the spermicide on one or both faces of the barrier and aong the circumference of the rim portion. However, since the rim must be squeezed by the user in order to insert the cervical barrier, it is not uncommon for the spermicide to be wiped clean from a substantial part of the barrier when it is being inserted into place. Thus, the effectiveness of the device is reduced.

Disposable contraceptive cervical barriers which include a spermicide embedded therein during manufacture of the barrier have been proposed. These are shown, for example, in U.S. Pat. Nos. 4,198,965 and 4,311,543 which issued to the present inventors and another. While such devices are believed to be a significant improvement in the art and are believed to be highly effective, there are those who prefer to use a cervical barrier which does not have a spermicide pre-impregnated therein. Furthermore, this decreases the cost of manufacture and distribution. It is also believed that many women will feel more secure by applying a spermicide themselves onto the cervical barrier.

SUMMARY OF THE INVENTION

The present invention is designed to overcome the disadvantages of the prior art and to provide an effective but inexpensive contraceptive cervical barrier which can be utilized once and then disposed of. The cervical barrier of the invention includes a bowl-shaped thin flexible member and a substantially thicker circular rim unitary with the flexible member. The rim provides a spring tension effect for helping to maintain the barrier in position. A plurality of cavities are formed in the rim and are equidistantly spaced therearound. The cavities are open so as to be capable of receiving and holding a quantity of a spermicide. Alternatively, the flexible member itself can be provided with a plurality of grooves for holding the spermicide. Preferably, the barrier is made from a mixture of a hydrophilic foam polymer and a more conventional polyurethane polyether prepolymer-catalyst system. The mixture is molded in a closed mold having a volume of about ten percent of the volume which the material would occupy if allowed to foam freely. The finished product is similar to an elastomer except that internally it has a dense cellular structure and is bounded by an impermeable skin.

BRIEF DESCRIPTION OF THE DRAWINGS

For the purpose of illustrating the invention, there are shown in the accompanying drawing forms which are presently preferred; it being understood that the invention is not intended to be limited to the precise arrangements and instrumentalities shown.

FIG. 1 is a front elevational view, partly in cross section, showing one embodiment of a disposable contraceptive cervical barrier constructed in accordance with the principles of the present invention;

FIG. 2 is a partial bottom plan view thereof;

FIG. 3 is a partial top plan view thereof;

FIG. 4 is a view similar to FIG. 1 showing a second embodiment of the invention;

FIG. 5 is a partial top plan view of the embodiment shown in FIG. 4;

DETAILED DESCRIPTION OF THE PREFERRED EMBODIMENTS

Figure 6:
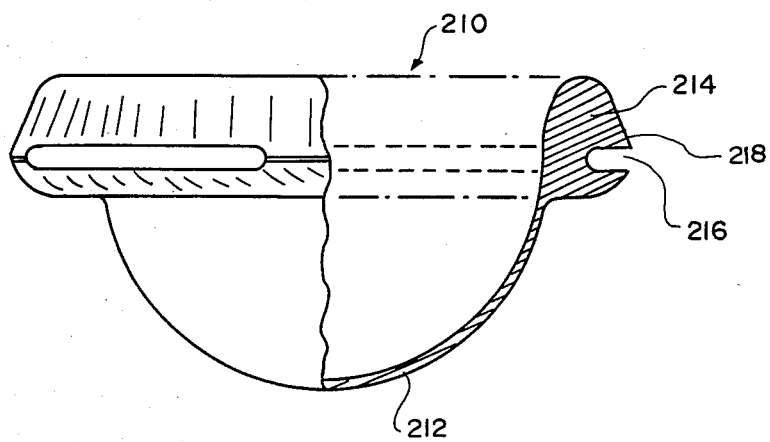
FIG. 6 is a view similar to FIGS. 1 and 4 showing a further embodiment.

Referring now to the drawings in detail wherein like reference numerals have been used throughout the various figures to designate like elements, there is shown in FIGS. 1, 2 and 3 a disposable contraceptive cervical barrier constructed in accordance with the principles of the present invention and designated generally as 10. The side, bottom and top of the cervical barrier 10 are shown respectively in FIGS. 1, 2 and 3.

As shown most clearly in FIG. 1, the cervical barrier includes a substantially bowl-shaped thin flexible member 12. The upper edge of the bowl-shaped member 12 is integrally connected with a substantially circular rim 14. The rim 14 is substantially thicker than the flexible member 12 and is preferably made from the same material in a single molding procedure which shall be described more fully hereinafter. As a result of the shape and density of the rim 14, the rim tends to remain in its circular configuration. As a result, it has a spring tension effect in that when the rim is squeezed toward its center axis it will tend to return to its original condition. This is most useful since the shape of the barrier must be distorted when it is being inserted into place but the rim must expand to its original position to act as a gasket as is known in the art.

The rim 14 itself is preferably substantially circular in cross section although the particular shape may be varied as desired. The rim, however, extends only outwardly of the bowl-shaped member so that the inner surface of the bowl adjacent the upper portion thereof is substantially smooth. That is, there are no projections extending inwardly of the bowl. Formed in the surface of the rim and substantially equally spaced therearound are a plurality of cavities or cells 16. In the embodiment shown in FIGS. 1, 2 and 3, the cells 16 are formed in the lower surface of the rim 14. This can be seen in FIGS.

1 and 2. The cells do not show in FIG. 3 as this is a top view. Thus, when viewing the barrier from the top, it will resemble conventional barriers.

The cavities or cells 16 are open so that a quantity of a spermicide in a gel, cream or foam form can be placed therein. The spermicide will be received in the cavity 16 and if the viscosity of the spermicide is properly selected, it will be held in the cavities by surface contact.

The disposable contraceptive cervical barrier 110 shown in FIGS. 4 and 5 is similar to the embodiment shown in FIGS. 1, 2 and 3. However, in this embodiment, the cavities 116 which are formed in the rim 114 are open at the top of the rim 114. There is, thus formed, a plurality of openings substantially equally spaced around the top surface of the rim portion as shown most clearly in FIG. 5. The purpose of the cavities in this embodiment is the same as with the first embodiment, i.e. to receive and hold a quantity of a spermicide.

A still further embodiment of the invention is shown in FIG. 6. The disposable contraceptive cervical barrier 210 of this embodiment also includes a substantially bowl-shaped thin flexible member 212 and a rim 214. As with the previous two embodiments, the rim includes a plurality of cavities 216 formed therein and substantially equidistantly located around the rim. The cavities 216, however, are formed so as to be open around the outermost edge or surface 218 of the rim 214.

With respect to each of the three embodiments described above, the number and size of each of the cavities may be varied to achieve the optimal effect. It should readily be apparent that the size and/or number of cavities must be great enough so that there will be a substantially continuous band or ring of the spermicide material around the rim. On the other hand, the individual cavities cannot be made too large or too close together since this would weaken the rim. As shown in the figures, the total volume of the cavities is substantially less than the volume of the remaining rim material.

Figure 7:
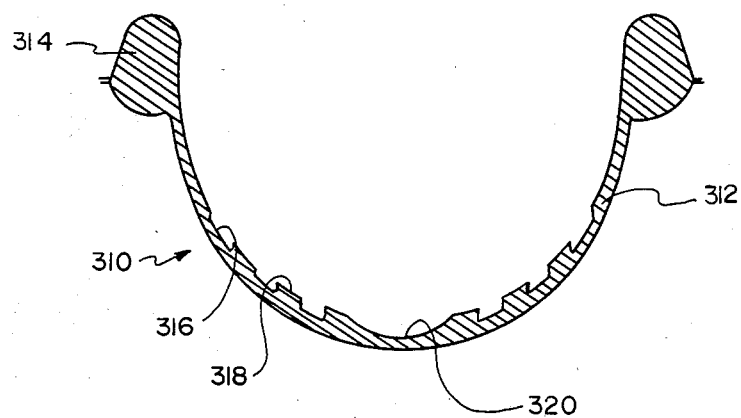
FIG. 7 is a cross-sectional view showing a still further embodiment of the invention.
Figure 8:
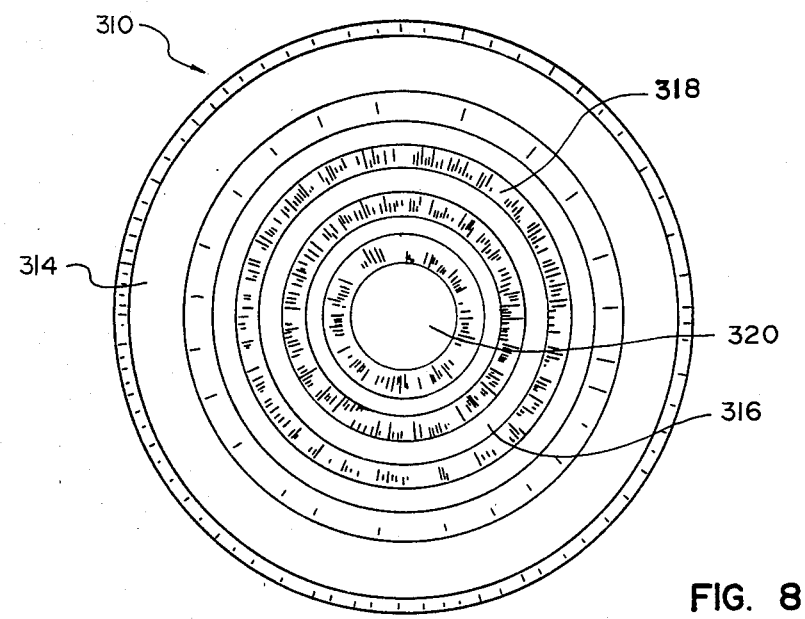
FIG. 8 is a top plan view of the embodiment shown in FIG. 8.

An even further embodiment of the invention is shown in FIGS. 7 and 8. In this embodiment, the bowl-shaped flexible member 312 of barrier 310 is provided with a plurality of shallow substantially concentric cavities 316 on the inner surface thereof. Located between each adjoining pair of grooves is a ridge 318 and a trough 320 lies at the middle of the barrier. The concentric grooves or cavities 316 are shown by way of example only as the same could be replaced with cavities of other shapes or with a spiral groove. Furthermore, the barrier 310 could also be provided with cavities in the rim 314 similar to the embodiments shown in FIGS. 1-6.

In use, a quantity of spermicide is placed into each of the cavities. An additional quantity of spermicide gel may also be placed around the other surfaces of the rim and the bowl-shaped flexible member as with conventional diaphragms. As the device is handled and particularly when the rim is squeezed so that the device can be inserted, some of the spermicide on the outer surface of the rim may be removed. However, because a quantity of spermicide is being held in the cavities, the effectiveness of the device remains extremely high.

The disposable contraceptive cervical barriers of the present invention are formed from urethane prepolymers. Actually, the prepolymer system of the invention is a blend of two different prepolymers. The first is "Hypol" which is a hydrophilic foam prepolymer manufactured by W. R. Grace Chemical Co. The second prepolymer is F-202 manufactured by Stepan Chemical Co.

The Hypol hydrophilic foam prepolymer, unlike conventional foam prepolymers, will accept and react with about 35 to 200 parts of water per 100 parts of prepolymer. With this prepolymer alone, the amount of water is not critical and does not have to be adjusted to the approximate stoichiometric equivalent of isocyanate content. Additionally, Hypol systems do not require a catalyst although the use of a catalyst will speed up the reaction.

The Stepan F-202 prepolymer is a conventional polyurethane polyether prepolymer typically designed to react with a catalyst system which contains triethylene diamine or a tin salt in a ratio of approximately 2.5 parts catalyst system to 100 parts prepolymer.

It has been found that the optimal percentage of the Hypol to the Stepan F-202 is approximately sixty percent Hypol to forty percent Stepan F-202. The combination of these two prepolymers produces a hydrophilic foam which, when molded under pressure, yields a disposable contraceptive cervical barrier the surface of which is relatively impermeable to the passage of water and whose circular rim is substantial enough to flex and return to its original shape. These properties allow the barrier to fit and perform properly.

Using this combination of prepolymers, it has been found that the product shows properties which are better than if either were used by itself. Typically, the F-202 prepolymer, by itself, would not even tolerate the large amounts of water used and would not produce a good foam. However, in this combination with the Hypol prepolymer and even with the larger amount of water, it forms a foam and contributes to the strength of the article. A product made in the same manner using just the Hypol prepolymer as the polymer component would not be nearly as strong and resilient and would not yield a surface having sufficient barrier properties to the passage of water.

A preferred composition for manuacturing products according to the invention is comprised of the following ingredients in the approximate percentages set forth:

| Ingredient | Percent by Weight |
| --- | --- |
| FHP-2002 Grace Prepolymer | 48.550 |
| F-202 Prepolymer Stepan | 32.370 |
| Surfactant 2270 Goldschmidt | 0.430 |
| Distilled Water | 18.150 |
| Nonoxynol - 9 | 0.150 |
| Preservative | 0.168 |
| Titanium Dioxide 3328 USP | 0.102 |
| Triethanolamine USP | 0.050 |
| Triethylenediamine | 0.030 |

Figure 9:
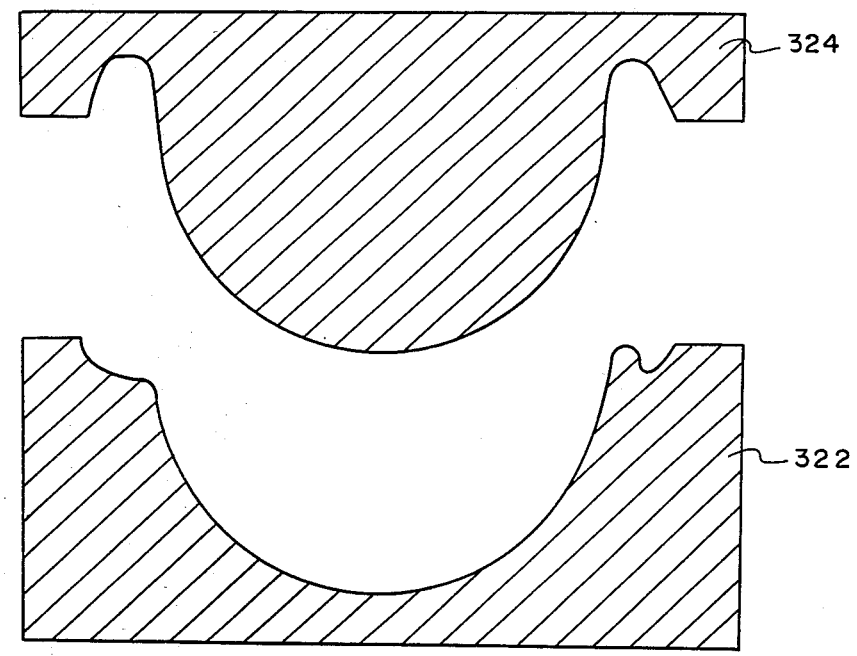
FIG. 9 is a schematic representation of a mold useful for producing disposable contraceptive cervical barriers in accordance with the present invention.

The above ingredients are prepared and mixed in a conventional manner using a standard meter-mix-dispense machine. The mixed material is then dispensed into the bottom half of a two-part mold such as mold half 322 shown in FIG. 9. The mold is then closed by lowering the upper mold half 324 so that a cavity is formed between the two mold halves which is substantially identical to the shape of the finished product. The mold halves are then held closed under sufficient pressure to keep them closed as the polymer material expands to fill the mold cavity.

The chemical reaction which takes place in the foaming, expanding and curing of the above formulation results in a product which is safe to use within the human body because of the extremely low levels of toluene di-isocyanate and toluene diamine. This apparently results from the relatively large amounts of water which is used.

The disposable contraceptive cervical barriers of the invention are molded under relatively high pressure. While the material within the mold expands to fill the mold, it expands to only a fraction of the space which it would occupy were it allowed to expand freely. The material would occupy a volume of approximately nine to ten times the volume of the molded article were it allowed to expand freely rather than be held in the mold. Furthermore, the material, if not molded under pressure, would absorb water freely.

Apparently as a result of being molded under pressure, the barrier of the present invention looks and feels like it is made of a solid elastomeric material. It is, however, cellular in structure. As shown in FIG. 1, the substantially bowl-shaped thin flexible member 12 is comprised of a dense cellular foam 18 and is covered by a continuous skin 20 which is formed of the same material except that it is less cellular in structure and more elastomeric in appearance. This skin or film 20 which lies on both the upper and lower surfaces is impermeable to water.

Another result of the high pressure molding is the simultaneous formation of the circular rim 14 which, due to the density of the material, has a great deal of resiliency. Unlike conventional diaphragms and other cervical barriers which use a circular rim insert to achieve the desired spring back effect, the cervical barrier of the present invention requires no such insert.

The present invention may be embodied in other specific forms without departing from the spirit or essential attributes thereof and accordingly, reference should be made to the appended claims rather than to the foregoing specification as indicating the scope of the invention.

We claim:

1. A disposable contraceptive cervical barrier comprising:
   a substantially bowl-shaped thin flexible member;
   a substantially circular rim portion unitary with said flexible member adjacent the upper portion thereof, said rim portion being substantially thicker than said flexible member and defining a means for achieving a spring tension effect;
   said rim portion extending only outwardly from said flexible member such that the inner surface of said bowl-shaped member adjacent the upper portion thereof is substantially smooth, and
   a plurality of cavities formed in said rim portion, said cavities being open so as to be capable of receiving and holding a quantity of a spermicide.

2. The invention as claimed in claim 1 wherein the total volume of said cavities is less than the volume of the remaining rim portion.

3. The invention as claimed in claim 1 wherein said cavities are substantially equidistantly spaced around said rim portion.

4. The invention as claimed in claim 3 wherein the openings for said cavities are located in the top surface of said rim portion.

5. The invention as claimed in claim 3 wherein the openings for said cavities are located in the bottom surface of said rim portion.

6. The invention as claimed in claim 3 wherein the openings for said cavities are located in the outermost surface of said rim portion.

7. A disposable contraceptive cervical barrier comprising:
   a substantially bowl-shaped thin flexible member;
   a substantially circular rim portion unitary with said flexible member, said rim portion being substantially thicker than said flexible member and defining a means for achieving a spring tension effect, and
   a plurality of cavities formed in said flexible member, said cavities being open so as to be capable of receiving and holding a quantity of a spermicide.

* * * * *